United States Patent [19]

Kraus et al.

[11] 4,392,960

[45] Jul. 12, 1983

[54] PROCESS FOR THE REMOVAL OF UREA FROM AQUEOUS SOLUTIONS

[75] Inventors: Menahem A. Kraus; Moshe A. Frommer, both of Rehovot; Mara Nemas, Neve Monoson; Rodika Gutman, Kiryat Sharet, all of Israel

[73] Assignee: A. T. Ramot Plastics, Ltd., Tel-Aviv, Israel

[21] Appl. No.: 652,812

[22] Filed: Jan. 27, 1976

[30] Foreign Application Priority Data

Jan. 27, 1975 [IL] Israel .......................... 46510
Jul. 15, 1975 [IL] Israel .......................... 47709

[51] Int. Cl.$^3$ .............................................. B01D 13/00
[52] U.S. Cl. ................................ 210/651; 210/654; 210/500.2
[58] Field of Search ............... 210/500 M, 23 H, 22, 210/651, 654, 500.2; 260/78 A, 78 R; 264/41

[56] References Cited

U.S. PATENT DOCUMENTS

| | | | |
|---|---|---|---|
| 3,228,877 | 1/1966 | Mahon | 210/22 |
| 3,567,632 | 3/1971 | Richter et al. | 210/23 H |
| 3,686,116 | 8/1972 | Rio | 210/500 M X |
| 3,822,202 | 7/1974 | Hoehn | 210/500 M X |
| 3,825,493 | 7/1974 | Brown et al. | 210/23 H |
| 3,899,309 | 8/1975 | Hoehn et al. | 210/500 M X |

OTHER PUBLICATIONS

McKinney et al. "Aromatic Polyamide Membranes for Preverse Osmosis Separation "*Macromolecules*", vol. 4, No. 5, Sep., Oct. 1971, pp. 633-637.
Lonsdule et al. "Study of Rejection of Various Solutes by R. O. Membranes," R & D Prog. Rept. No. 447, 7/69, U.S. Dept. of Interior Contract No. 14-01-00-01-1717.
Agrawal et al., "Specification, Selectivity, and Performance of Porous Cellulose Acetate Membranes in Reverse Osmosis," *I & EC Process, Design and Development*, vol. 8, No. 4, Oct. 1969, pp. 439-449.
Amore et al., "Research on Reverse Osmosis Membranes for Purification of Wash Water at Sterilization Temperature (165° F.)" *Office of Saline Water Report* No. 815 (1972), Abstract Page.
Wydeven et al., "Performance of Cellulose Acetate Butyrate Membranes in Hyper-filtration of Sodium Chloride and Urea Feed Solution," *Journal of Applied Polymer Science*, vol. 17, pp. 2277-2287 (1973).
Lawrence et al., "Development of a Reverse Osmosis Module for Wash Water Recycling in a Space Environment at 165° F.", *Office of Saline Water Report* No. 905 (INT-OSW-RDPA-74-905), (1974), cover page and pp. 8 and 9.
Poist et al., "Development of Improved PBI Membrane Systems for Wash Water Recycling at Pasteurization Temperatures," *Office of Saline Water Report* No. 995, (1974), cover page and pp. 40-41.
Gregor et al., "Synthetic-Membrane Technology," *Scientific American*, vol. 239, pp. 112-128, Jul. 1978.

*Primary Examiner*—Frank A. Spear, Jr.
*Attorney, Agent, or Firm*—Browdy & Neimark

[57] ABSTRACT

A process for the removal of urea from an aqueous solution containing same, which comprises subjecting the solution to reverse osmosis through a polymeric membrane prepared from a polymer of the formula

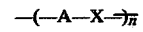

wherein
A designates an aromatic moiety and
X designates a bivalent linking group, the aromatic moiety A being chosen from the group consisting of phenyl, biphenyl, naphthyl, and mixtures of such moieties; and such moieties connected by means of linkages selected from —O—, —SO$_2$—, —SO—, —NH—, —CH$_2$—, and —PO(R) (wherein R is alkyl); mixtures of aromatic and aliphatic chains of not more than 6 carbon atoms which do not constitute above 40 mole-% of the A-groups; mixtures of aromatic and alicyclic moieties wherein the alicyclic moieties do not constitute more than 50 mole-% of the A-groups; mixtures of aromatic and heterocyclic moieties, wherein said A moieties are optionally substituted by one or more substituents selected from the group consisting of alkyl of up to 4 carbon atoms, alkoxy of up to 4 carbon atoms, amino, dialkylamino, hydroxy, carboxy, carboxamido and sulfonic acid; the group X being selected from amido (—NH—CO—), substituted amido (—NR—CO—) wherein R is lower alkyl, provided that the substituted amido groups do not constitute more than 50 mole-% of the X groups; hydrazido (—CO—NH—NH—CO—), ureido (—NH—CO—NH—), semicarbazido (—NH—CO—NH—NH—CO—), sulfonamido (—SO$_2$—NH—), and phosphoramido of the formula —CO—NH—Ar—NH—PO(NHAr)—NH—Ar—NH—CO and mixtures of the above linking groups, and wherein n is about 80 to 300, and devices for the hyperfiltration of urea-containing aqueous solutions, whenever based on the above process and on membranes defined above.

1 Claim, No Drawings

PROCESS FOR THE REMOVAL OF UREA FROM AQUEOUS SOLUTIONS

FIELD OF THE INVENTION

The present invention relates to a novel process for the separation of urea, possibly together with other metabolites and also with salts, from aqueous solutions containing these, by means of reverse osmosis through suitable membranes. The invention further relates to a process for the separation of urea and other solutes from aqueous solutions and especially from body fluids. The invention also relates to certain novel membranes for such separation processes, to a process for the production of such membranes and to devices for effecting such separation processes. Furthermore, the invention relates to novel membranes for the separation of various low molecular weight solutes, including urea, from aqueous solutions and to separation processes based on reverse osmosis by means of such novel membranes. The invention also relates to novel polymers which are useful in the preparation of membranes of the type defined above. The invention also relates to novel types of membranes having a substantially increased rate of filtration, as compared with membranes known hitherto, and to the preparation of these. Other and further features of the invention will become apparent hereinafter.

We have found that certain types of membranes, some of which were used hitherto for desalination and for the sweetening of water, can be used effectively for the separation of urea from aqueous solutions containing it. Hitherto, generally no satisfactory separation of urea has been achieved by means of various desalination membranes tried out for this purpose. We have found that when certain inorganic or organic compounds are incorporated into the material from which the membranes are prepared, substantially increased rates of flow can be obtained. The quantities of the compounds incorporated are much larger than thought hitherto to give satisfactory results, and the results obtained by the incorporation of such large quantities are better than those of the known membranes.

PRIOR ART

Considerable developments have been made during recent years in the desalination of seawater and of brackish water by reverse osmosis. Little has been done in the application of similar techniques for the removal of urea from aqueous solutions, and especially from body fluids. Interest has been shown in a process for the removal of urea from urine and wash water in space flight (J.App.Pol.Sci. 17 (1973),2277). A process of this type is of value in the development of light-weight artificial kidneys (U.S. Pat. No. 3,579,441, U.S. Pat. No. 3,799,873; U.S. Pat. No. 3,825,493, German Pat. App. P No. 2321168.9; P No. 2321188.3). In such devices, the purification from accumulated metabolites is effected by hyperfiltration (reverse osmosis) of water used for dialysis, and the thus purified water may be used for further dialysis. The polymer generally used for the preparation of desalination membranes is cellulose acetate. Membranes of this type are characterized by a high salt rejection, but by only a poor rejection of urea, (See Lonsdale et al., Office of Saline Water, R & D Progress Report No. 447 (1969). It is probable that the mechanism of urea transfer through such membranes differs from that of salts. As compared with a 45% urea rejection by cellulose acetate membranes, cellulose triacetate films gave a 66% rejection (OSW R&D Progress Report 447). Still better results were obtained with heat treated cellulose acetate butyrate membranes which gave a 85% urea rejection from 1% feed solution at a filtration rate of 1.75 gfd (gallons per square foot per day) at 600 psi (J.Appl. Pol. Sci. 17 (1973) 2277). Recently certain aromatic polymers with nitrogen-containing linking groups were suggested for desalination, and these are reported to have better mechanical properties than cellulose acetate (U.S. Pat. No. 3,567,632). A single report deals with the rejection of urea by a membrane of this type having polyamide groups and aromatic moieties, and this was stated to be about 92% from 1.8% feed solution at a filtration rate of 6 gfd at 600 psi: McKinney, Macromolecules 4 633 (1971).

The polymer from which these membranes were prepared is of the formula —NH—$\phi$—CO—NH—$\phi$—NHCO—$\phi$—CO where $\phi$ designates a phenylene group and such polymer is prepared in a three-stage synthesis. An additional report concerning these membranes indicates different results: 70.5% urea rejection and a flux of 2.34 gfd at 600 psi: J.App.Pol.Sci. 17 (1973) 2277.

Porous glass was reported to reject 91.6% urea from a 1% solution but this was at a flow rate of only 0.26 gfd, at 1200 psi and depends to a large extent on the specific batch of glass. The results obtained according to the present invention are better than those of the known processes, a higher rejection is obtained and furthermore the membranes according to the present invention can be produced in a simple manner, as will be set out hereinafter.

SUMMARY OF THE INVENTION

The process according to the present invention comprises effecting the removal of urea—possibly together with other solutes—from an aqueous solution of same, inclusive of body fluids, by reverse osmosis effected by means of a polymeric membrane prepared from a polymer of the type

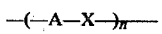

wherein
A designates an aromatic group and
X designates a bivalent linking group, the aromatic group being a group such as penyl, biphenyl, naphthyl, or a mixture of such groups, or such groups connected by means of linkages such as —O—, —SO$_2$—, —SO—, —NH—, —CH$_2$—, —PO(R) (wherein R is alkyl); or a mixture of aromatic and aliphatic groups such aliphatic chains of not more than 6 carbon atoms which do not constitute above 40 mole-% of the A-groups; or a mixture of aromatic and alicyclic groups wherein the alicyclic moieties do not constitute more than 50 mole-% of the A-groups; or a mixture of aromatic and heterocyclic groups; said groups A possibly being substituted by one or more substituents selected from alkyl of up to 4 carbon atoms, alkoxy of up to 4 carbon atoms, amino, dialkylamino, hydroxy, carboxy, carboxamido and sulfonic acid groups; the group X being selected from amido (—NH—CO—), substituted amido (—N-R—CO—) wherein R is lower alkyl, provided that the substituted amido groups do not constitute more than 50 mole-% of the X groups; hydrazido (—CO—NH—NH—CO—), ureido (—NH—CO—NH—), semicarbazido (—NH—CO—NH—NH—CO—), or sulfonamido (—SO₂—NH—), or mixtures of the above linking groups, and wherein n is about 80 to 300.

Some of the polymers and membranes prepared from such polymers are known from desalination, see for example U.S. Pat. No. 3,567,632.

The present invention further relates to novel polymers and to membranes prepared from these. The novel polymers are of the general formula $$-(A-X')_n-$$

wherein A is as defined above and wherein X' designates a phosphoramido group (—CO—NH—Ar—NH—PO(NHAr)—NH—Ar—NH—CO—) or a mixture of amido, hydrazido, semicarbazido or ureido moieties together with phosphoramido moieties. The polymers for the membranes of the present invention are prepared by a number of processes. Amongst these there may be mentioned the polycondensation at low temperatures, in a manner similar to the reaction described in U.S. Pat. No. 3,567,632. According to one of the embodiments of the invention, the polyamide polymers are prepared by dissolving a suitable aromatic diamine, or mixture of aromatic diamines, or an aromatic phosphoramide diamine, in a suitable solvent, such as N,N-dimethylacetamide, cooling the solution to a temperature of about −10° to −30° C., adding an aromatic diacid chloride (or a mixture of such chlorides) either in solid form or as solution, mixing at the low temperature for a predetermined period of time and allowing the reaction mixture to warm up to ambient temperature or above. After completion of the reaction to a degree of at least about 95%, the liberated hydrogen chloride is neutralized by the addition of a base such as pyridine and the polymer is precipitated by pouring the reaction mixture into an ice water mixture in which it is insoluble. The precipitate is washed and dried under reduced pressure.

Membranes are cast from the polymer dissolved in a suitable solvent, or they may be cast directly from the reaction mixture defined above. Amongst suitable solvents there may be mentioned N,N-dimethylacetamide, dimethyl sulfoxide or hexamethyl phosphoramide. Preferably, the solvents contain certain salts which exert a favorable effect on the membranes prepared and which increase the rate of flux through these. Certain organic additives can also be used. The cast membranes may be precipitated in a non-solvent, such as water, or the solvent may be first partially evaporated at a suitable temperature and pressure, and the membrane is then precipitated. The membranes are suitable for the rejection of urea, possibly together with other solutes, and at a urea concentration of about 5000 ppm. and at 600 psi operating pressure the urea rejection is at least 60%. In many cases a rejection better than 95% can be attained, and this is considerably better than the rejection possible hitherto by similar processes. The membranes are characterized by a high rejection of urea and they are also effective in rejecting low molecular weight compounds such as inorganic salts from aqueous solutions.

Hyperfiltration of Solutions Containing Urea

Membranes prepared as described above can be used in stirred, high pressure reverse osmosis cells, flow-through cells, plate and frame membrane stacks or other devices usually used in reverse osmosis processes, or in artificial kidney devices as described in U.S. Pat. No. 3,579,441. The solutions containing urea can be filtered through such membranes at pressures exceeding the osmotic pressure of such solutions (generally over 10 atm.). The concentration of urea in the permeate does not exceed 40% of that of the feed solution and generally is very much lower. As the membranes of this invention are also effective desalination membranes, salts, sugars, and other solutes contained in the feed solution are also rejected to a large extent. The permeate thus contains a low concentration of solutes and—if used, for example, in conjunction with an artificial kidney device—may be reused for further dialysis.

The addition of certain low molecular weight compounds, which may be inorganic or organic, to the solutions from which the membrane is cast, results in a substantial increase in the rate of flow through membranes prepared from such solutions. The flux increases generally with an increase of the quantity of the compounds incorporated into the casting solutions, and this up to a certain content of such additives. Concentrations of up to 150% calculated on the polymer in the solution may be used with good results. In U.S. Pat. No. 3,567,632 certain limitations of salt concentrations have been given, and the high quantities of such additives used according to the present invention are contrary to the teaching of the prior art and give better results. Hitherto, lithium chloride and lithium nitrate were considered to be effective additives, but contrary to this teaching there are provided according to the present invention additives which give better results. Amongst these there may be mentioned various compounds of aluminum, lanthanum, magnesium, thorium, and zinc which are compatible with the system of polymer and solvent from which the membranes are prepared. Amongst these there may be specifically mentioned nitrates of aluminum, lanthanum and thorium, perchlorates, such as magnesium perchlorate and lithium perchlorate, chlorides such as lithium chloride which is preferably used in combination with a suitable organic additive; alkali metal isocyanates such as KCNS, chlorides such as zinc chloride and magnesium chloride. It is clear that these are only examples and that other suitable inorganic salts and compounds can be used which are compatible with the above defined system and which increase the rate of flux through the membrane produced therefrom. The inorganic additives are advantageously used in combination with organic additives, as such combinations result in further improvements. Amongst organic compounds which may be used by themselves or which may be used in combination with inorganic additives there may be mentioned acetamide, pyridine hydrochloride, guanidine hydrochloride and the like. Generally the additives are used in quantities of from about 10% to about 35% weight/volume calculated on the polymer solution. As generally solutions of about 20% of the polymer are used, it is clear that the higher ratios constitute up to about 150% or even more calculated on the polymer in the solution. It will become apparent from the following results that the higher ratios of additives result in higher rates of flux through the membranes.

Where not indicated otherwise in the following Examples, the membranes were cast from solutions containing 20% w/v of the polymer. The quantities of the additives are calculated on the solution, and thus it is clear that quite high percentages of these additives were used.

DESCRIPTION OF PREFERRED EMBODIMENTS

EXAMPLES

EXAMPLE I

Polymerization of a Mixture of meta- and para-Phenylenediamine with iso-phthaloyl Chloride (Polymer MP-M)

A mixture of 5.4 gr (50 mmol) of m-phenylenediamine and 5.4 gr (50 mmol) of p-phenylenediamine is dissolved in 112 ml of dry N,N-dimethylacetamine under dry nitrogen. The solution is cooled to $-20°$ C. and 20.3 gr (100 mmol) of solid isophthaloyl chloride are added in portions of about 5 gr. The viscous mixture obtained is stirred at $-20°$ C. for 15 minutes, warmed gradually to room temperature and 17.7 ml (200 mmol) of dry pyridine are added. Part of the polymer is precipitated by pouring into ice-water in a blender. The precipitate is washed thoroughly with water and alcohol, air-dried and finally dried in a vacuum oven at 80° C.

EXAMPLE II

Membrane Preparation and Characterization

Membranes are cast either directly from the reaction mixture of Example I containing 18% w/v of pyridine hydrochloride or from redissolved polymer. When prepared from the reaction mixture, the solution is stored (usually for at least 24 hours) before casting, so as to let gas bubbles escape. When preparing membranes from redissolved polymer, a 10–20% solution (W/W) of the polymer in dimethylacetamide containing a suitable additive is prepared. The solution is filtered through sintered stainless steel and stored for at least 24 hours.

Membranes are cast at a thickness of 0.2–0.5 mm on a clean, dry glass plate. The plate with the cast solution is placed in an oven at the desired temperature for a predetermined period. The membrane is then coagulated by immersing the plate into distilled water at room temperature. The membrane performance is tested after at least 24 hr storage in water. In Table I are summarized some performance data of membranes prepared from the polymer of Example I under various conditions.

TABLE I

Urea Rejection of Membranes Prepared from Polymer MP-M under Various Conditions[a], additive: 5% w/v LiCl

| Oven Temp. (°C.) | Oven Time (hr.) | Urea Rejection (%) | Filtration Rate gfd |
|---|---|---|---|
| 80 | 1 | 58 | 1.65 |
| 80 | 2 | 62 | 1.20 |
| 90 | 1 | 75 | 1.05 |
| 110 | 1 | 84 | 0.75 |

[a]Membranes were prepared from MP-M polymer precipitated and redissolved in dimethylacetamide —5% LiCl to give a 20% solution; casting thickness was 0.4mm, final: about 0.1 mm. Feed solution concentration was 0.5% urea. Pressure: 50 atm.

Membranes prepared directly from the reaction mixture of polymer MP-M and heated at 90° C. for 1 hour exhibited a rejection of 92% with a filtration rate of 1.74 gfd.

EXAMPLE III

Polymerization of m-Phenylenediamine with a Mixture of tere- and iso-Phthaloyl Chloride and Membrane Preparation. (Polymer M-MP)

The polymer is prepared by a procedure as described in Example I. Membrane performance data are summarized in Table II.

TABLE II

Urea Rejection of Membranes Prepared from Polymer M-MP under Various Conditions[a]

| Polymer Solution Concentration (%) | Oven Temp. (°C.) | Oven Time (hour) | Urea Rejection (%) | Filtration Rate (gfd) |
|---|---|---|---|---|
| 20 | 90 | 0.5 | 75 | 1.35 |
| 20 | 90 | 1 | 96 | 1.20 |
| 10 | 90 | 1 | 42 | 2.55 |
| 10 | 90 | 2 | 73 | 2.25 |

[a]Membranes were prepared directly from the reaction mixture. Casting thickness 0.4 mm, final thickness: 0.1 mm. Feed solution concentration was 0.5%, Pressure - 50 atm.

EXAMPLE IV

Polymerization of m-Phenylenediamine with iso Phthaloyl Chloride and Membrane Preparation. (Polymer MM)

The polymer and membranes are prepared as described in Examples I and II. Membrane performance data are summarized in Table III.

TABLE III

Urea Rejection of Membranes Prepared from Polymer MM under Various Conditions[a]

| Casting Thickness (mm) | Oven Temp. (°C.) | Oven Time (hr) | Urea Rejection | Filtration Rate |
|---|---|---|---|---|
| 0.2 | 80 | 2 | 78 | 1.20 |
| 0.4 | 90 | 1 | 86 | 1.70 |

[a]Pressure 50 atm. solution concentration 20%.

EXAMPLE V

Hyperfiltration of Various Urea Containing Solutions Through Aromatic Polyamide Membranes In Table IV are summarized data on the hyperfiltration of various solutions through membranes prepared from Polymer M-MP. These data show that the presence of other solutes does not appreciably affect the rejection of urea.

TABLE IV

Hyperfiltration of Complex Solutions

| Composition of Filtered Solution | Filtration Rate (gfd) | Solute Rejection | | |
|---|---|---|---|---|
| | | Urea | NaCl | Creatinine |
| 5000 ppm urea | 1.12 | 95 | — | — |
| 5000 ppm urea 5000 ppm NaCl 1000 ppm Creatinine | 1.12 | 95 | 97 | 99 |
| 5000 ppm urea 30000 ppm NaCl | 0.9 | 94 | 97 | |

EXAMPLE VI

Hyperfiltration of Peritoneal Dialysis Solutions

The membranes of this invention may be used for purification of spent peritoneal dialysis solutions by hyperfiltration. In these filtrations rejection for urea and other nitrogen-containing metabolites is at least as high as with simple binary solutions, as shown in Table V.

TABLE V

| Hyperfiltration of Spent Peritoneal Dialysate with a M-MP Membrane | | |
|---|---|---|
| Solution | Urea Rejection % | Filtration Rate (gfd) |
| Peritoneal dialysate | 92 | 1.74 |
| 5000 ppm urea | 89 | 1.65 |

EXAMPLE VII

Polymerization of para Aminobenzhydrazide with Isophthaloyl Chloride, Membrane Preparation and Characterization Para-aminobenzhydrazide and isophthaloyl chloride were polymerized as described in Example I. Membranes were prepared essentially as described in Example II but were then heat treated. Thus a membrane heated at 100° for 1 hr exhibited a urea rejection of 65% (0.5% feed solution, 50 atm) while an untreated member rejected only 12% urea.

EXAMPLE VIII

Polymerization of p,p'-Diaminodiphenylsulfone with Isophthaloyl chloride, Membrane Preparation and Characteristics p,p'-Diaminodiphenylsulfone and isophthaloyl chloride were polymerized at low temperature as described in Example I. Membranes were prepared as described in Example II. In hyperfiltration of 0.5% urea solution through such a membrane at 50 atm, urea rejection was 88% and filtration rate 0.15 gfd.

EXAMPLE IX

Polymerization of Piperazine with Isophthaloyl Chloride and Membrane Preparation Piperazine may be polymerized with isophthaloyl chloride by interfacial polycondensation following L. Credali et al, Desalination, 14, 137 (1974). Membranes are cast from formic acid solutions. Membranes which are cast at a thickness of 0.4 mm and evaporated at 60° for 30 minutes show urea rejections of 80–89% and filtration rates of 1.0–1.5 gfd. (0.5% urea feed, 50 atm).

EXAMPLE X

Polymerization of 4,4'-Diaminodicyclohexyl methane with Isophthaloyl Chloride 4,4'-Diaminodicyclohexyl methane was polymerized with isophthaloyl chloride in dimethylacetamide solution as described in Example I. Membranes of 0.4 mm casting thickness, evaporated for 30 min. at 90°, show urea rejections of 75–85% and filtration rates of 0.7–1.1 gfd (0.5% urea feed, 50 atm).

EXAMPLE XI

Polymerization of 4,4'-Diamino-3,3'-dimethyldiphenyl methane with a Mixture of Iso- and Terephthaloyl chloride 4,4'Diamino-3,3'-dimethyldiphenyl methane is polymerized with a mixture of iso- and terephthaloyl chloride as described in Example I. Membranes prepared by casting at a thickness of 0.4–0.5 mm and evaporated for 30'–60' at 90° exhibit urea rejections of 75–85% and filtration rates of 0.7–1.3 gfd (0.5% urea feed solution; 50 atm).

EXAMPLE XII

Polymerization of 3,3'-Diaminoglutaroyldianilide with Isophthaloyl Chloride, Membrane Preparation and Characterization 3,3'-diaminoglutaroyl dianilide was polymerized with isophthaloyl chloride in analogous quantities and under the same conditions as set out in Example I. Membranes were prepared from the reaction mixture by casting: 0.4 mm thickness upon casting, 1 hour evaporation at 90° C. A rate of water flux of 0.135 gfd and a 42% urea rejection was attained at 50 atm.

EXAMPLE XIII

Polymerization of a Mixture of m-Phenylenediamine and 3,3'-Diamino-N,N',N''-triphenylphosphorictriamide with Isophthaloyl Chloride; Membrane Preparation and Characterization A mixture of 10% (by weight) of 3,3'-diamino-N,N',N''-triphenyl phosphoric triamide and 90% of m-phenylene diamine was polymerized with isophthaloyl chloride as described in Example I and a 10% polymer solution was obtained. A membrane was prepared from this solution by casting (0.4 mm thickness upon casting, 10 minutes in a vacuum oven at 90° C.) and this gave an 87% urea rejection and a filtration rate of 2.6 gfd. A membrane prepared in a similar manner from 5% of the above phosphoramide and 95% of the phenylenediamine gave a 70% urea rejection and 3.6 gfd filtration rate at 50 atm.

EXAMPLE XIV

Polymerization of a Mixture of 3,5-Diaminobenzoic Acid and m-Phenylenediamine with Isophthaloyl Chloride, Membrane Preparation and Characterization Substitution of 10 to 20% of the amine component in polymerizations according to Example I by 3,5-diaminobenzoic acid brings about an increase in filtration rates of the thus prepared membranes. For example, a mixture containing 20% by weight diaminobenzoic acid resulted in a membrane with a filtration rate of 3.0 gfd and an urea rejection of 73% at 50 atm. A MP-M membrane prepared under identical conditions gave a filtration rate of 1.2 gfd and an urea rejection of 85%.

EXAMPLE XV

Preparation of MP-M Membranes under Reduced Pressure

The preparation of MP-M Membranes (according to Example I), in a vacuum oven resulted in a substantial decrease of the time necessary for oven treatment. Increased filtration rates were obtained, without affecting urea rejection, as evident from the following Table.

TABLE VI

| MP-M Membranes prepared in Vacuum Oven | | | | |
|---|---|---|---|---|
| Oven Temp. °C. | Oven Time minutes | Filtration Rate (gfd) - 50 atm | Rejection | |
| | | | Urea | NaCl |
| 110 | 10 | 1.5 | 86 | 96 |
| 90 | 10 | 3.0 | 86 | 97 |

EXAMPLE XVI

Preparation of Membranes from Solutions Containing Additives

Membranes were prepared from solutions containing various additives. The casting thickness was 0.4 mm and the membranes were treated in an oven during 1 hour or in a vacuum oven during 10 minutes. These were compared with similar membranes prepared under identical conditions but without additives. Without additives an average rejection of urea of 85% and a flow rate of 0.02 gfd was obtained (both with and without vacuum evaporation). Performance of membranes prepared with additives was:

TABLE VII

MP-M Membranes prepared with Pyridine Hydrochloride, 1 hour, 90° C.

| Concentration | | Urea | Filtration |
|---|---|---|---|
| % w/v | molarity | Rejection (%) | Rate (gfd) - 50 Atm |
| 5 | 0.43 | 80 | 0.15 |
| 10 | 0.86 | 80 | 0.30 |
| 20 | 1.72 | 85 | 1.2 |

Further membranes were prepared in a regular non-vacuum oven. Results are given in the following Table VIII.

TABLE VIII

Effect of Additives on MP-M Membranes (prepared in regular oven) 1 hour, 90° C.

| Additive | Concentration | | Filtration | Rejection | |
|---|---|---|---|---|---|
| | % w/v | Molarity | Rate (gfd) | NaCl | Urea |
| $ZnCl_2$ | 5 | 0.36 | 0.45 | 93 | 72 |
| $ZnCl_2$ | 10 | 0.72 | 1.1 | 99 | 83 |
| $ZnCl_2$ + | 10 | 0.73 | | | |
| | | | 2.2 | 99 | 88 |
| $C_5H_5N.HCL$ | 18 | 1.56 | | | |
| $Mg(ClO_4)_2$ | 10 | 0.44 | 0.9 | 96 | 72 |
| $MgCl_2$ + | 10 | 0.44 | | | |
| | | | 4.5 | 99 | 80 |
| $C_5H_5N.HCl$ | 18 | 1.56 | | | |

TABLE IX

Effect of Additives on MP-M Membranes (prepared in vacuum oven); 10 min, 5 mm Hg

| Additive | Concentration | | Filtration | Rejection (%) | |
|---|---|---|---|---|---|
| | % w/v | Molarity | Rate (gfd) | NaCl | Urea |
| KCNS + | 10 | 1.03 | 1.65 | 89 | 74 |
| $C_5H_5N.HCl$ | 18 | 1.56 | | | |
| $Mg(ClO_4)_2$ + | 5 | 0.22 | 5.7 | | 78 |
| $C_5H_5N.HCl$ | 18 | 1.56 | | | |
| $Al(NO_3)_3$ + | 10 | 0.47 | 6.0 | — | 79 |
| $C_5H_5N.HCl$ | 18 | 1.56 | | | |
| $Th(NO_3)_4$ + | 10 | 0.21 | 5.7 | 98 | 79 |
| $C_5H_5N.HCl$ | 18 | 1.56 | | | |
| $La(NO_3)_3$ + | 15 | 0.46 | 5.3 | — | 75 |
| $C_5H_5N.HCl$ | 18 | 1.56 | | | |
| Thiourea | 5 | 0.66 | 0.06 | — | 25 |
| $Li(ClO_4)$ | 5 | 0.47 | 0.98 | 97 | 85 |
| LiCl + | 5 | 1.2 | | | |
| | | | 2.2 | 95 | 66 |
| Acetamide | 10 | 1.44 | | | |

The process according to the present invention of removing urea, possibly together with other metabolites and salts from aqueous solutions, and especially from body fluids, can be effected by any conventional device used for this purpose. Any type of artificial kidney can be advantageously used with membranes of the type defined in this patent specification and due to the high rejection rates and due to the comparatively high rates of flux through the membranes advantageous results are obtained. What we claim is:

1. A process for the removal of urea from an aqueous solution containing same, wherein a removal equivalent to a rejection of at least 60% from a urea concentration of 5,000 ppm and at 600 psi operating pressure is achieved, which comprises subjecting the solution to reverse osmosis through a polymeric membrane produced from a polymer obtained by the polymerization of m-phenylenediamine, 3,3'-diamino-N,N',N"-triphenyl phosphoric triamide and isophthaloyl chloride.

* * * * *